United States Patent
Hsu et al.

(10) Patent No.: US 6,410,784 B1
(45) Date of Patent: Jun. 25, 2002

(54) RECOVERY OF METAL COMPONENTS OF A CATALYST IN A PROCESS FOR PRODUCTION OF TRIMELLITIC ACID

(75) Inventors: Hsi-Yen Hsu; Ching-Tang Lin, both of Hsinchu (TW)

(73) Assignee: Chinese Petroleum Corporation (TW)

( * ) Notice: Subject to any disclaimer, the term of this patent is extended or adjusted under 35 U.S.C. 154(b) by 0 days.

(21) Appl. No.: 09/835,670

(22) Filed: Apr. 16, 2001

(51) Int. Cl.[7] .......................... C07C 51/16; B01J 20/34; B01J 38/62; B01J 31/00
(52) U.S. Cl. ...................... 562/414; 562/404; 502/28; 502/170
(58) Field of Search ................................. 562/414, 409

(56) References Cited

U.S. PATENT DOCUMENTS

| | | | |
|---|---|---|---|
| 4,719,311 A | * | 1/1988 | Partenheimer et al. |
| 4,786,752 A | | 11/1988 | Holzhauer et al. .......... 562/414 |
| 4,816,601 A | | 3/1989 | Lowry et al. ............... 562/413 |

* cited by examiner

Primary Examiner—Paul J. Killos
Assistant Examiner—Farhad Forohar
(74) Attorney, Agent, or Firm—Ostrolenk, Faber, Gerb & Soffen, LLP

(57) ABSTRACT

A process for recovering cobalt and manganese components from a product stream or a residue stream that resulted from a process which employs a catalyst system containing the cobalt and manganese components for oxidizing pseudocumene to trimellitic acid includes the steps of adding a precipitating agent to the product stream or the residue stream in an effective amount to react with the cobalt and manganese components in the product stream or the residue stream.

6 Claims, No Drawings

RECOVERY OF METAL COMPONENTS OF A CATALYST IN A PROCESS FOR PRODUCTION OF TRIMELLITIC ACID

BACKGROUND OF THE INVENTION

1. Field of the Invention

This invention relates to a process for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream.

2. Description of the Related Art

U.S. Pat. No. 4,786,752 discloses a method for recovery and recycle of metal components of a catalyst system from a residual stream that resulted from a manufacturing process for the production of trimellitic acid (TMLA) from pseudocumene in an acid solvent, such as acetic acid and mixture of acetic acid and water. The catalyst system contains cobalt, manganese and bromine components, or cobalt, manganese, zirconium and bromine components. The residue stream is a molten bottom stream that resulted from distillation of a product stream of trimellitic anhydride in the aforesaid process, and contains the bromine component and essentially all the metal components of the catalyst.

The aforesaid method for recovery of the metal components from the residue stream involves the steps of addition of water to the residue stream to form an aqueous solution, and addition of a precipitating agent of an oxalic acid compound to the aqueous solution to precipitate the metal components in the aqueous solution as oxalate salts. Reaction of oxalic acid with the metal components is influenced by the concentration of the reactants, the pH value, and temperature of the medium.

U.S. Pat. No. 4,816,601 discloses the aforementioned manufacturing process for the production of trimellitic anhydride. The manufacturing process also involves a step of precipitating the aforesaid metal components of the catalyst system by addition of the oxalic acid compound in the product stream prior to the separation of trimellitic anhydride from the product stream.

The disclosures mentioned in the aforementioned patents are incorporated herein by reference in their entireties.

SUMMARY OF THE INVENTION

The object of the present invention is to provide a process that employs different precipitating agents to replace the aforesaid oxalic acid compound for the recovery of the metal components from the aforementioned residue stream. These precipitating agents are highly active to precipitate the aforesaid metal compounds.

According to one aspect of the present invention, a recovering process is provided for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream. The recovering process comprises: adding 2,3-pyridine dicarboxylic acid to the product stream or the residue stream in an effective amount to react with the cobalt and manganese components in the product stream or the residual stream so as to form a precipitate of cobalt and manganese 2,3-pyridine dicarboxylates in the product stream or the residual stream; and separating the precipitate of cobalt and manganese 2,3-pyridine dicarboxylates from the product stream or the residual stream.

According to another aspect of the present invention, a recovering process is provided for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream. The recovering process comprises: adding 2-aminobenzoic acid to the product stream or the residue stream in an effective amount to react with the cobalt and manganese components in the product stream or the residual stream so as to form a precipitate of cobalt and manganese 2-aminobenzoates in the product stream or the residual stream; and separating the precipitate of cobalt and manganese 2-aminobenzoates from the product stream or the residual stream.

According to yet another aspect of the present invention, a recovering process is provided for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream. The recovering process comprises: adding pyromellitic dianhydride to the product stream or the residue stream in an effective amount to react with the cobalt and manganese components in the product stream or the residual stream so as to form a precipitate of cobalt and manganese pyromellitic dicarboxylates in the product stream or the residual stream; and separating the precipitate of cobalt and manganese pyromellitic dicarboxylates from the product stream or the residual stream.

According to still another aspect of the present invention, a recovering process is provided for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream. The recovering process comprises: adding tartaric acid to the product stream or the residue stream in an effective amount to react with the cobalt and manganese components in the product stream or the residual stream so as to form a precipitate of cobalt and manganese tartrates in the product stream or the residual stream; and separating the precipitate of cobalt and manganese tartrates from the product stream or the residual stream.

DETAILED DESCRIPTION OF THE PREFERRED EMBODIMENTS

As mentioned in the aforesaid U.S. Pat. No. 4,786,752, and U.S. Pat. No. 4, 816,601 the recovery of metal components, i.e. cobalt and manganese, is significantly influenced by the concentration of the oxalic acid compound, the pH value, and temperature of the medium. However, nothing was taught in the aforesaid patents that there are suitable precipitating agents other than the oxalic acid compound that are as effective as the oxalic acid compound to precipitate the metal components from the product stream that resulted from the aforesaid manufacturing process or the residue stream that resulted from the distillation of the trimellitic acid (TMLA). In fact, it has been found that there is no clear evidence that shows a predictable group of compounds as effective precipitating agents for the recovery of the metal components by simply being analogous to the oxalic acid compound.

The inventors surprisingly found that 2,3-pyridine dicarboxylic acid, 2-aminobenzoic acid, pyromellitic dianhydride, and tartaric acid are as effective as the oxalic acid compound for the recovery of the metal components.

The present invention will be described in more detail in the following Examples.

EXAMPLES 1 to 12

Examples 1 to 12 are experiments employing the 2,3-pyridine dicarboxylic acid, 2-aminobenzoic acid, pyromellitic dianhydride, and tartaric acid as precipitating agents for the recovery of the cobalt and manganese from an aqueous solution which simulates the aqueous solution formed in the recovery method disclosed in the aforesaid U.S. Pat. No. 4,786,752. The aqueous solution of each Example is prepared by adding $Co(OAc)_2 \cdot 4H_2O$, $Mn(OAc)_2 \cdot 4H_2O$, and a bromine compound, such as HBr and NaBr, into water in the presence or absence of acetic acid.

Table 1 shows the amount of the components used for preparing the aqueous solution and the recovery yields of the cobalt and manganese for each of these Examples.

With the invention thus explained, it is apparent that various modifications and variations can be made without departing from the spirit of the present invention. It is therefore intended that the invention be limited only as recited in the appended claims.

We claim:

1. A recovering process for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream, comprising the steps of:

adding 2,3-pyridine dicarboxylic acid to the product stream or the residue stream in an effective amount to react with the cobalt and manganese components in the product stream or the residual stream so as to form a precipitate of cobalt and manganese 2,3-pyridine dicarboxylates in the product stream or the residual stream; and separating the precipitate of cobalt and manganese 2,3-pyridine dicarboxylates from the product stream or the residual stream.

2. The recovering process of claim 1, further comprising a step of adding water to the product stream or the residual stream before the step of adding 2,3-pyridine dicarboxylic acid to the product stream or the residual stream.

3. A recovering process for recovering cobalt and manganese components from a product stream that resulted from a manufacturing process of oxidizing pseudocumene to trimellitic acid in an acetic acid medium in the presence of a catalyst system containing the cobalt and manganese

TABLE 1

| Example | Acetic acid (g) | $H_2O$ (g) | $Co(OAc)_2 \cdot 4H_2O$ (g) | $Mn(Oac)_2 \cdot 4H_2O$ (g) | Bromine compound (g) | Precipitating agent (g) | Co recovery yield % | Mn recovery yield % |
|---|---|---|---|---|---|---|---|---|
| 1 | 100 | 100 | 8.595 | 4.589 | HBr 2.044 | A1* 23.906 | 89.08 | 78.13 |
| 2 | 0 | 200 | 9.032 | 4.346 | HBr 2.187 | A1 23.529 | 74.31 | 46.76 |
| 3 | 0 | 200 | 8.561 | 4.615 | NaBr 2.112 | A1 23.621 | 83.68 | 67.55 |
| 4 | 100 | 100 | 8.644 | 4.273 | HBr 2.094 | A2** 21.336 | 99.87 | 56.34 |
| 5 | 0 | 200 | 8.757 | 4.395 | HBr 2.155 | A2 21.336 | 99.19 | 76.59 |
| 6 | 0 | 200 | 8.332 | 4.298 | NaBr 1.965 | A2 21.336 | 99.96 | 88.82 |
| 7 | 100 | 100 | 8.525 | 4.763 | HBr 2.295 | A3# 34.902 | 94.94 | 64.04 |
| 8 | 0 | 200 | 8.435 | 4.376 | HBr 2.223 | A3 34.074 | 94.44 | 70.23 |
| 9 | 0 | 200 | 8.280 | 4.653 | NaBr 2.859 | A3 35.047 | 96.32 | 63.98 |
| 10 | 100 | 100 | 8.815 | 4.556 | HBr 2.093 | A4+ 26.400 | 99.13 | 99.91 |
| 11 | 0 | 200 | 8.679 | 4.725 | HBr 2.191 | A4 26.268 | 99.40 | 99.99 |
| 12 | 0 | 200 | 8.814 | 5.036 | NaBr 2.151 | A4 26.078 | 99.08 | 99.99 |

*A1 represents Tartaric acid.
**A2 represents 2-aminobenzoic acid.
A3 represents Pyromellitic dianhydride.
+A4 represents 2,3-pyridine-dicarboxylic acid.

components, or from a residue stream that resulted from distillation of the aforesaid product stream, comprising the steps of:

adding 2-aminobenzoic acid to the product stream or the residue stream in an effective amount to react with the cobalt and manganese components in the product stream or the residual stream so as to form a precipitate of cobalt and manganese 2-aminobenzoates in the product stream or the residual stream; and separating the precipitate of cobalt and manganese 2-aminobenzoates from the product stream or the residual stream.

4. The recovering process of claim 3, further comprising a step of adding water to the product stream or the residual stream before the step of adding 2-aminobenzoic acid to the product stream or the residual stream.

5. A recovering process for recovering cobalt and manganese components from a product stream that resulted from a manufacturing process of oxidizing pseudocumene to trimellitic acid in an acetic acid medium in the presence of a catalyst system containing the cobalt and manganese components, or from a residue stream that resulted from distillation of the aforesaid product stream, comprising the steps of:

adding tartaric acid to the product stream or the residue stream in an effective amount to react with the cobalt and manganese components in the product stream or the residual stream so as to form a precipitate of cobalt and manganese tartrates in the product stream or the residual stream; and separating the precipitate of cobalt and manganese tartrates from the product stream or the residual stream.

6. The recovering process of claim 5 further comprising a step of adding water to the product stream or the residual stream before the step of adding tartaric acid to the product stream or the residual stream.

* * * * *